(12) United States Patent
Kapoor

(10) Patent No.: US 11,166,768 B2
(45) Date of Patent: Nov. 9, 2021

(54) 3D PRINTED ROBOT FOR HOLDING MEDICAL INSTRUMENTS DURING PROCEDURES AND ITS CONTROL

(71) Applicant: Siemens Healthcare GmbH, Erlangen (DE)

(72) Inventor: Ankur Kapoor, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 297 days.

(21) Appl. No.: 16/086,164

(22) PCT Filed: May 26, 2017

(86) PCT No.: PCT/EP2017/062733
§ 371 (c)(1),
(2) Date: Sep. 18, 2018

(87) PCT Pub. No.: WO2017/203026
PCT Pub. Date: Nov. 30, 2017

(65) Prior Publication Data
US 2020/0222126 A1    Jul. 16, 2020

Related U.S. Application Data

(60) Provisional application No. 62/341,841, filed on May 26, 2016.

(51) Int. Cl.
*A61B 34/30* (2016.01)
*B33Y 80/00* (2015.01)
(Continued)

(52) U.S. Cl.
CPC .............. *A61B 34/30* (2016.02); *B25J 18/00* (2013.01); *B33Y 80/00* (2014.12);
(Continued)

(58) Field of Classification Search
CPC ..... B29C 64/153; B29C 64/129; B33Y 80/00; B25J 18/00; B29L 2031/7546;
(Continued)

(56) References Cited

U.S. PATENT DOCUMENTS 5,397,323 A    3/1995  Taylor et al.
5,410,638 A *  4/1995  Colgate ................ B25J 17/0216
                                                  700/260
(Continued)

FOREIGN PATENT DOCUMENTS

EP    2153793 A2    2/2010
EP    3106678 A1    12/2016
(Continued)

OTHER PUBLICATIONS

Lessard, S., Bigras, P., and Bonev, I. A. (Oct. 19, 2007). "A New Medical Parallel Robot and Its Static Balancing Optimization." ASME. J. Med. Devices. Dec. 2007; 1(4): 272-278. (Year: 2007).*

(Continued)

*Primary Examiner* — William J Levicky
*Assistant Examiner* — Alexander M Eisenberg

(57) ABSTRACT

A system for holding and controlling medical instruments during procedures includes an end effector configured to hold a medical instrument and a rotational and translational (RT) mechanism configured to rotate and translate the medical instrument along an insertion axis. The system further includes a platform coupled to the RT mechanism and a pair of parallel five-bar planar linkages configured to translate, pitch, and yaw the platform with respect to a principal axis that is parallel to the insertion axis.

12 Claims, 11 Drawing Sheets

(51) Int. Cl.
  *B25J 18/00* (2006.01)
  *A61B 34/20* (2016.01)
  *B29L 31/00* (2006.01)
  B29C 64/153 (2017.01)
  B29C 64/129 (2017.01)

(52) U.S. Cl.
  CPC ............... *A61B 2034/2048* (2016.02); *A61B 2034/2065* (2016.02); *A61B 2034/304* (2016.02); *A61B 2562/0261* (2013.01); *B29C 64/129* (2017.08); *B29C 64/153* (2017.08); *B29L 2031/7546* (2013.01)

(58) Field of Classification Search
  CPC ............... E05D 11/1007; E05D 11/10; Y10T 16/54024; Y10T 16/54247; Y10T 5/4028; A61B 34/30; A61B 2034/2048; A61B 2034/2065; A61B 2034/304; A61B 2562/0261; A61B 90/50; A45B 25/02
  See application file for complete search history.

(56) References Cited

U.S. PATENT DOCUMENTS

| | | | |
|---|---|---|---|
| 5,944,736 A * | 8/1999 | Taylor | A61B 17/0206 606/198 |
| 6,047,610 A * | 4/2000 | Stocco | B25J 17/0266 74/479.01 |
| 7,021,173 B2 | 4/2006 | Stoianovici et al. | |
| 8,469,945 B2 | 6/2013 | Schena | |
| 8,506,556 B2 | 8/2013 | Schena | |
| 2004/0216277 A1* | 11/2004 | Beaver | E06C 1/32 16/324 |
| 2011/0297196 A1* | 12/2011 | Durante | A45B 17/00 135/15.1 |
| 2014/0121675 A1* | 5/2014 | Bax | A61B 90/11 606/130 |
| 2015/0164596 A1* | 6/2015 | Romo | A61B 1/0016 604/104 |
| 2015/0320514 A1* | 11/2015 | Ahn | A61B 34/30 606/130 |
| 2016/0074120 A1* | 3/2016 | Farritor | A61B 17/2812 606/130 |

FOREIGN PATENT DOCUMENTS

| | | |
|---|---|---|
| GB | 2522446 A | 7/2015 |
| WO | WO2014198784 A1 * 12/2014 | ............ A61B 17/15 |

OTHER PUBLICATIONS

International Search Report dated Dec. 22, 2017 in corresponding International Application No. PCT/EP2017/062733.
Entsfellneret al.: "First 3D printed medical robot for ENT surgery—Application specific manufacturing of laser sintered disposable manipulators"; 2014 IEEE/RSJ International Conference On Intelligent Robots and Systems; IEEE; pp. 4278-4283.
J. Funda, R. H. Taylor, B. Eldridge, S. Gomory, and K. G. Gruben, Constrained cartesian motion control for teleoperated surgical robots, IEEE Transactions on Robotics and Automation 12 (1996), No. 3, 453-465.
S. Hutchinson, G. D. Hager, and P. I. Corke, A tutorial on visual servo control, IEEE Transactions on Robotics and Automation 12 (1996), No. 5, 651-670.
A. Kapoor, Ming Li, and R. H. Taylor, Constrained control for surgical assistant robots, Proceedings 2006 EEE International Conference on Robotics and Automation, 2006. ICRA 2006., May 2006, pp. 231-236.
A. Kapoor and R. H. Taylor, A constrained optimization approach to virtual fixtures for multi-handed tasks, Robotics and Automation, 2008. ICRA 2008. IEEE International Conference on, May 2008, pp. 3401-3406.
R. Kumar, P. Berkelman, P. Gupta, A. Barnes, P. S. Jensen, L. L. Whitcomb, and R. H. Taylor, Preliminary experiments in cooperative human/robot force control for robot assisted microsurgical manipulation, Robotics and Automation, 2000. Proceedings. ICRA '00. IEEE International Conference on, vol. 1, 2000, pp. 610-617 vol. 1.
Ming Li, A. Kapoor, and R. H. Taylor, A constrained optimization approach to virtual fixtures, 2005 IEEE/RSJ International Conference on Intelligent Robots and Systems, Aug. 2005, pp. 1408-1413.
Russell Taylor, Pat Jensen, Louis Whitcomb, Aaron Barnes, Rajesh Kumar, Dan Stoianovici, Puneet Gupta, ZhengXian Wang, Eugene Dejuan, and Louis Kavoussi, A steady-hand robotic system for microsurgical augmentation, The International Journal of Robotics Research 18 (1999), No. 12, 1201-1210.
L. Weiss, A. Sanderson, and C. Neuman, Dynamic sensor-based control of robots with visual feedback, IEEE Journal on Robotics and Automation 3 (1987), No. 5, 404-417.

* cited by examiner

3D PRINTED ROBOT FOR HOLDING MEDICAL INSTRUMENTS DURING PROCEDURES AND ITS CONTROL

CROSS-REFERENCE TO RELATED APPLICATIONS

This application claims the benefit of U.S. Provisional Application Ser. No. 62/341,841 filed May 26, 2016, which is incorporated herein by reference in its entirety.

TECHNICAL FIELD

The present disclosure relates generally to methods, systems, and apparatuses associated with a 3D printed robot for holding medical instruments during procedures and the control of that robot.

BACKGROUND

Traditionally industrial and medical robots have been constructed out of metal parts that are individually machined. Though this leads to a very precise mechanism, it adds to the cost as it does not use manufacturing for scale. With the current state of art of 3D printing (additive manufacturing), it is possible to produce production quality parts with an accuracy of sub-millimeters. In such processes the parts are made by fusing plastic materials layer-by-layer either through lithography or laser sintering. These processes are ideal for manufacturing low volume plastic parts. However, since the part is produced in layers, the accuracy diminishes as the depth/vertical dimension of the part increases. Thus a complex mechanism such as a robot intended to hold a medical instrument with sufficient accuracy is a challenging engineering and technical task.

SUMMARY

Embodiments of the present invention address and overcome one or more of the above shortcomings and drawbacks, by providing methods, systems, and apparatuses related to 3D printed robots for holding medical instruments during procedures. Briefly, the 3D printed robots described herein include a disposable linkage component which can be discarded after a fixed number of uses and a reusable assembly. In some embodiments, the 3D printed robots include control mechanisms with embedded sensors and images, bearing in mind the accuracy of printed parts.

According to some embodiments, a system for holding and controlling medical instruments during procedures includes an end effector configured to hold a medical instrument and a rotational and translational (RT) mechanism configured to rotate and translate the medical instrument along an insertion axis. The system further includes a platform coupled to the RT mechanism and a pair of parallel five-bar planar linkages configured to translate, pitch, and yaw the platform with respect to a principal axis that is parallel to the insertion axis. These linkages may be, for example, planar linkages, spherical linkages, or some combination thereof.

Additionally, in one embodiment, the system further includes an inertial sensor embedded in the platform or the end effector, as well as a set of strain gauges mounted on a coupling between the end effector and the RT mechanism. The system may then be controlled based on user input received via the strain gauges and/or measurements received via the inertial sensor. In another embodiment, the system includes an external imager configured to acquire one or more images during the procedure, and the system is controlled at least in part using the acquired images.

One or more of the components of the aforementioned system (e.g., the platform, linkages, etc.), may be fabricated using additive manufacturing techniques. In some embodiments, the fabricated parts may be grouped into sub-assemblies joined via a magnetically power rapid connect-disconnect coupling or other coupling mechanism. For example, in one embodiment, there are two such sub-assemblies: a first sub-assembly of reusable parts comprising the end effector, the RT mechanisms, and the platform, and a second sub-assembly of disposable parts comprising the pair of parallel five-bar planar linkages. In this way, the second sub-assembly can be readily removed and replaced as needed after use within the system.

Some embodiments of the aforementioned system include a motor box comprising a plurality of motors configured to provide motion inputs to the pair of parallel five-bar planar linkages. This motor box may be coupled to the other components of the system, for example, using a magnetic powered quick connect-disconnect mechanism. The system may use additional motors and other mechanisms to facilitate motion of different system components. For example, in one embodiment, additional motors mounted on the platform and configured to provide motion inputs to the RT mechanism. Motion inputs may be provided to the RT mechanism using a cable or belt running parallel to the pair of parallel five-bar planar linkages.

According to other embodiments of the present invention, a hinge joint capable of being printed in a printed configuration and used in a deployed configuration includes an inner hinge member and an outer hinge member. The inner hinge member includes a follower component comprising a top portion and a bottom portion, and splines spaced unevenly around the top portion and the bottom portion of the follower component. The outer hinge member comprising a top base component comprising a first set of grooves distributed around an interior portion of the top base component, and a bottom base component comprising a second set of grooves distributed around an interior portion of the bottom base component. The follower component interconnects with the outer hinge member between the top base component and the bottom base component when in the printed configuration or the deployed configuration. The first set of grooves and the second set of grooves are spaced such that (a) the splines align with the grooves when the hinge joint is in the printed configuration and (b) the splines do not align with the grooves when the hinge joint is in the deployed configuration.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at methods, systems, and apparatuses related to 3D printed robots for holding medical instruments during procedures. In some embodiments, a pair of five bar parallel linkages is used to locate and orient a platform on which a rotational and translation mechanism is mounted. In the other embodiments, a five bar spherical linkage is used to locate and orient a platform about a remote center of motion. Both the designs used in the embodiments described above may be optimized such that they can be manufactured with current 3D printing techniques and plastics. This implies that the design must respect the limited load bearing capabilities, accuracy and the layered manufacturing process of 3D printed parts. The control architecture of these parts is also unique as it must also take into consideration the limits of the accuracy of parts produced by incorporating measurements of the observed scene and the partial observations on the orientation of the platform attached to the five-bar mechanisms.

Traditional control architecture for robots assumed that the mechanism itself is fairly accurate and backlash free. Therefore measurement of joint angles is sufficient to obtain an accurate estimate of the end effector location and orientation. A 3D printed mechanism on the other hand, has inaccuracies that may vary between different batches of parts produced as well as backlash between hinges or joints. The techniques described herein overcome this by use of an embedded sensor that measures part of the observations of the end-effector. Additionally, a hybrid control employing observations from images may be applied to enhance the overall positional accuracy of the mechanism chain.

Figure 1:
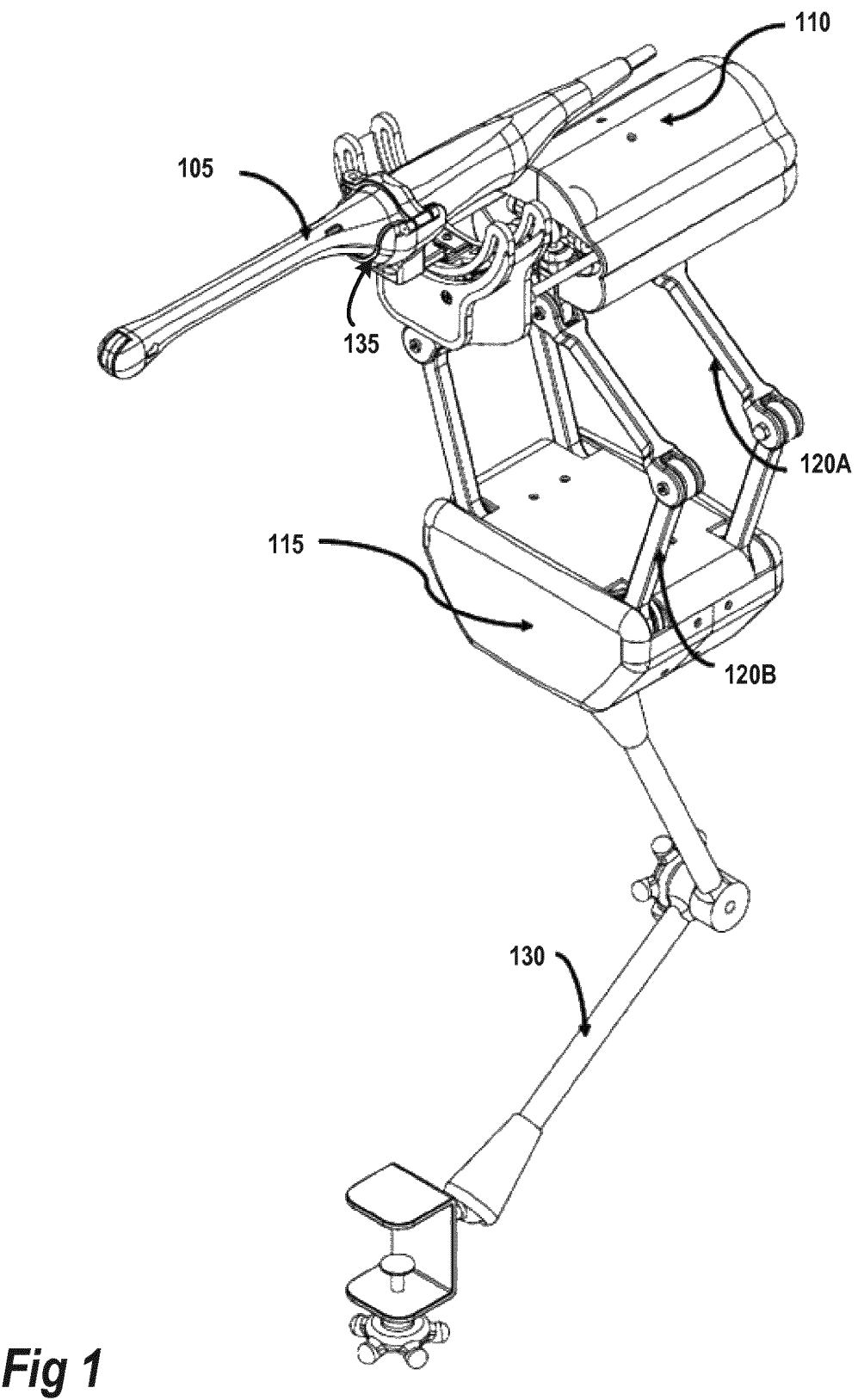
FIG. 1 provides an overview of a 3D printed robot, according to some embodiments.

FIG. 1 provides an overview of a 3D printed robot, according to some embodiments. A Medical Device 105 (e.g., an ultrasound transducer or surgical tool) is held in an End Effector 135 which, in turn, is connected to a Rotational and Translational (RT) Mechanism 110. The RT Mechanism 110 is connected to two linkage assemblies, or "Linkages," 120A, 120B which facilitate movement of the Medical Device 105 by the RT Mechanism 110. A Motor Box 115 houses one or more motors which adjust the positioning of the Linkages 120A, 120B. A Passive Arm 130 is used to provide further adjustment of placement of the Medical Device 105 during its use in medical applications. In some embodiments, the robot can comprise a plurality of sub-assemblies. For example, in one embodiment, the sub-assemblies may include a first sub-assembly of reusable parts comprising the End Effector 135, the RT Mechanism 110, and a platform (described below), as well as a second sub-assembly of disposable parts comprising the Linkages 120A, 120B. Where multiple sub-assemblies are used, they may be joined via a magnetically power rapid connect-disconnect coupling or any similar technique for coupling 3D parts generally known in the art.

Figure 2A:
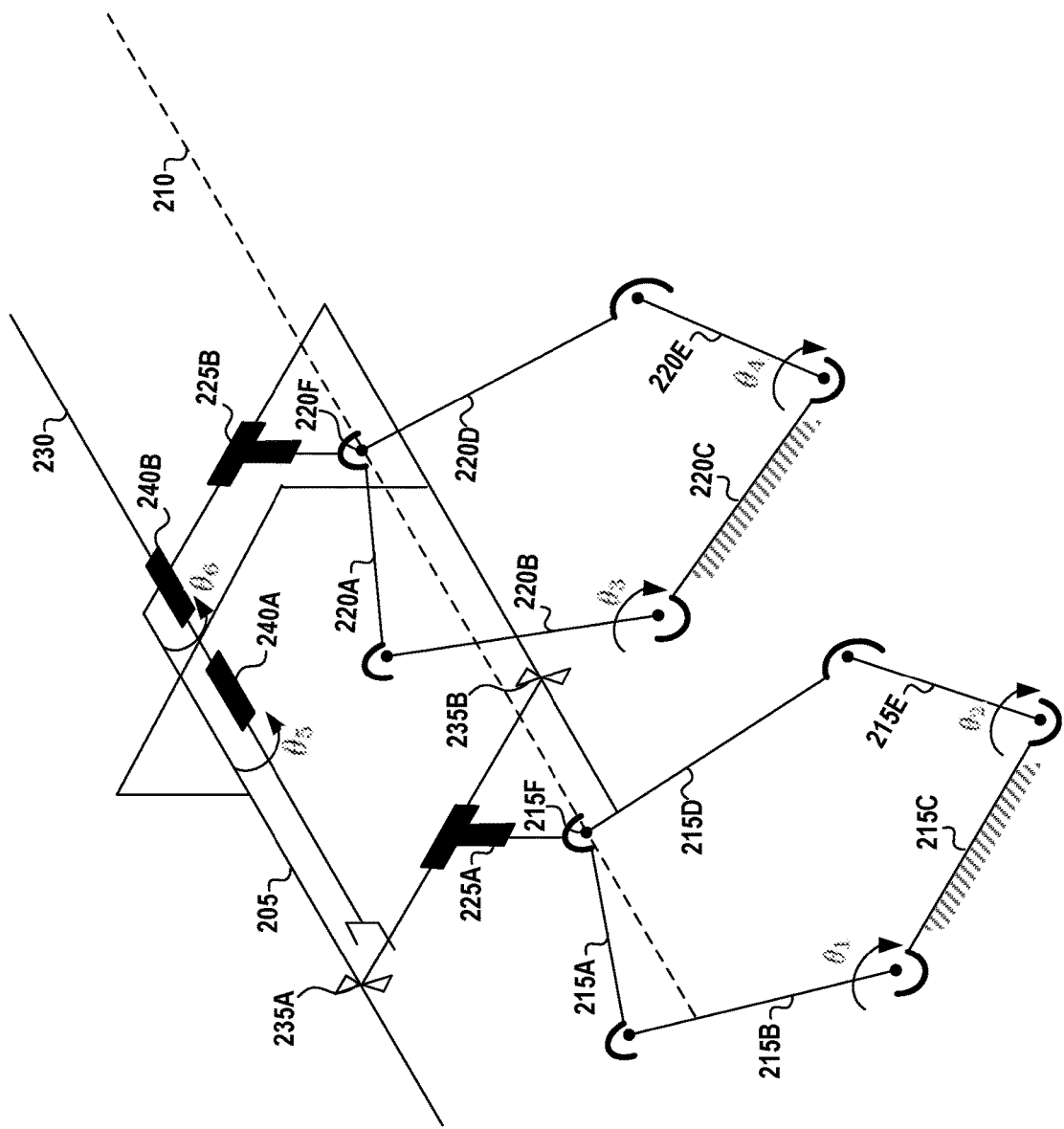
FIG. 2A is a schematic representation of the kinematics of the 3D printed robot, as it may be implemented in some embodiments.

FIG. 2A is a schematic representation of the kinematics of the 3D printed robot, as it may be implemented in some embodiments. It shows the relationships of links and pivot connections, as well as the two rotational joints that are coupled to produce the translation and rotation of the end effector along its axis. There are two sets of links and pivots forming two planar five bar linkage mechanisms. The first planar five bar linkage mechanisms comprises Links 215A, 215B, 215C, 215D, 215E and Pivot 215F (collectively, "Linkage A"). The second planar five bar linkage mechanism comprises Links 220A, 220B, 220C, 220D, 220E and Pivot 220F (collectively, "Linkage B").

Linkage A and Linkage B are coupled via a Platform 205 that can yaw (i.e., move along a vertical yaw axis) and pitch (i.e., move along a lateral pitch axis). The angulation of the four joints (labeled $\theta_1$ to $\theta_4$) of each five bar linkage mechanism control the lateral position, yaw, and pitch of this Platform 205. Angles $\theta_1$ and $\theta_2$ control the position of the Pivot 215F in Linkage A, while angles $\theta_3$ and $\theta_4$ control the position of Pivot 220F in Linkage B. The vector from Pivot 215F to Pivot 220F determines the yaw and pitch of the Platform 205. The line joining Pivot 215F and Pivot 220F is the Principal Axis 210.

Two Degrees-of-Freedom Mechanisms 240A, 240B are attached to this Platform 205. These Two Degrees-of-Freedom Mechanisms 240A, 240B are coupled together to produce a rotation and translational motion of the end effector along the Principal Axis 210. In this embodiment, the Insertion Axis 230 given by the axis of these two degrees-of-freedom is parallel to the Insertion Axis 230 with an offset. However, it must be noted that the kinematics of the mechanism do not change if there is no offset or the Insertion Axis 230 is not parallel to the Principal Axis 210. In FIG. 2A, Offset Links 225A and 225B are attached to Links 215A and 220A, respectively, to offset the Platform 205 from the Principal Axis 210. Another mechanism with the same kinematics can be generated where the offsets from Pivots 215F and 220F are different or even zero. The placement of the Insertion Axis 230 outbound from the Principal Axis 210 may be beneficial to allow the ultrasound transducer or surgical tool to be supported and manipulated without interfering with the motion of the mechanism. It may also simplify the installation, removal and sterilization construction of the transducer or surgical tool holder.

The Two Degrees-of-Freedom Mechanisms 240A, 240B generate a rotational and translational motion of the end effector. In one embodiment, two motor actuators with gear heads can be mounted on the RT mechanism itself. This makes the mechanism modular with applications to other designs. In another embodiment, all six motor actuators with gear heads are mounted on the base Links 215C and 220C. Since the separation between Pivot 215F and Prismatic Joints 235A and 235B may change based on the angulation of the Platform 205, power is transmitted along Linkage B. This is accomplished, for example using a cable and pulley system or a belt and sprocket system. The latter has the advantage of providing no slippage and backlash free motion. The belt system must be able to accommodate non-parallel axes for drive and driven sprockets. The belt comprises a single core with cogs attached to it at a certain pitch. In either case, groves are incorporated along the links to guide the cables or pulleys. In this embodiment, a motor may be mounted parallel to another motor and its power transmission is via Link 215D and 215E of Linkage A (or Link 220D and 220E of Linkage B). An third motor may be mounted parallel to a fourth motor and its power runs along Link 215A and 215B of Linkage A (or Link 220A and 220B of Linkage B).

Figure 2B:
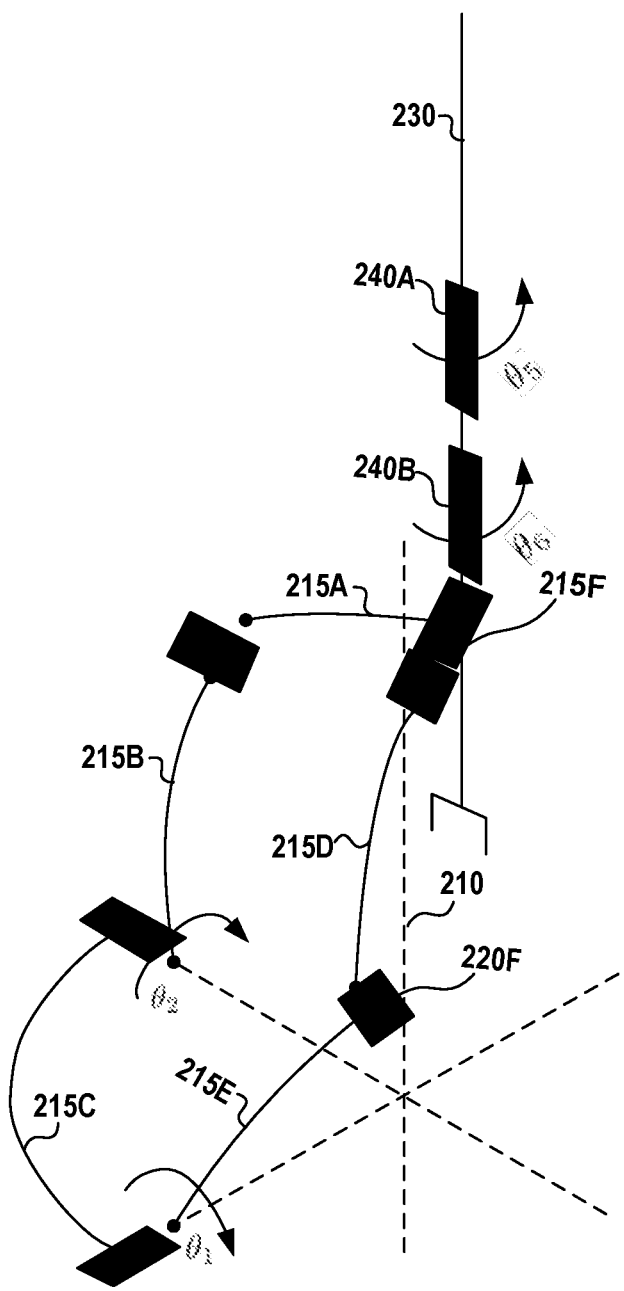
FIG. 2B is a schematic representation of the kinematics of the robot holder for endoscopic applications, as it may be used in some embodiments.

FIG. 2B is a schematic representation of the kinematics of the robot holder for endoscopic applications, as it may be used in some embodiments. It shows the relationships of links and pivot connections (using reference numbers from FIG. 2A), as well as the Two Degrees-of-Freedom Mechanisms 240A, 240B that are coupled to produce the translation and rotation of the end effector along the Insertion Axis 230. The links themselves may have irregular shape to accommodate placement of pivoted connections and the pivots can pass one another without collision. The linkage will function as a spherical linkage as long as the axes of the pivoted connections all pass through a common center. In other words, the end of the link is a geodesic on a sphere of certain radius, and the pivots are tangents at the end points of the link. Every sphere corresponding to each link is concentric with their center as the remote center of spherical rotation. In some embodiments, each of these spheres is designed with a different radius to allow the link to pass freely without collision with each other.

The final link in the kinematics of the mechanism are two rotational degrees-of-freedom which are coupled together to produce a rotation and translational motion of the end effector along the axis given by the Pivot 4 and the center of the rotation. This is the Principal Axis 210 of the mechanism. The two degrees-of-freedom represented by $\theta_3$ and $\theta_4$ are aligned parallel with the Principal Axis 210. In this embodiment, there is no offset between the axis of two degrees-of-freedom called the Insertion Axis 230 and Principal Axis 210. However, it must be noted that the kinematics of the mechanism does not change if there is another link attached to either Link 215A or 215D, offsetting the insertion axis from the Principal Axis 210. The insertion axis may have an angular offset with the Principal Axis 210, such that the center of the link attached to either of Link 215A or 215D is tangential to the sphere corresponding to this attached link.

Preferably the Insertion Axis 230 has no offset from the Principal Axis 210 to result in a compact mechanism that can be directly 3D printed without requiring significant assembly. For example, the five spherical links can be directly printed along with pivots as one piece. The remaining two degrees-of-freedom mechanism is printed separately and assembled to the five bar linkage mechanism. An additional benefit of have no offset is in means of supplying actuation power to these two degrees-of-freedom. In one embodiment, two motor actuators with gear heads can be mounted on the rotational and translation mechanism itself. This makes the mechanism modular with applications to other designs.

Figure 3A:
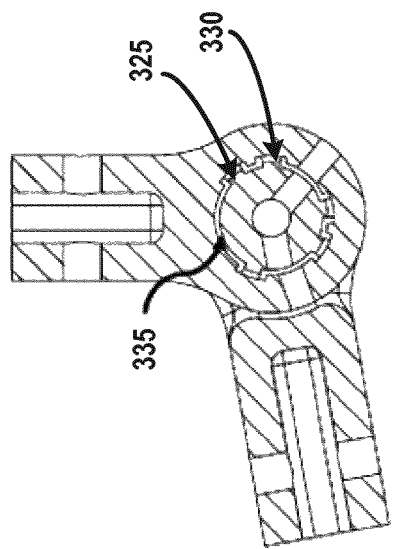
FIG. 3A shows an illustration of the hinge joint for the linkage assemblies in a printed configuration, according to some embodiments.
Figure 3A:
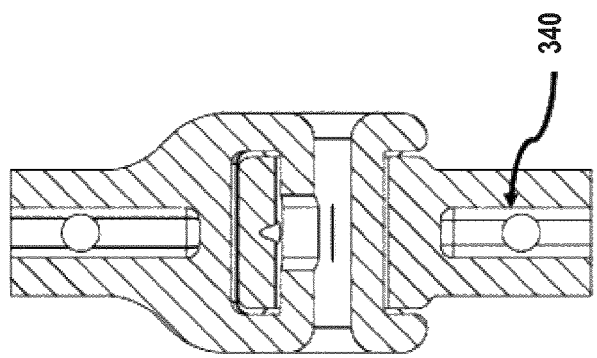
Figure 3A:
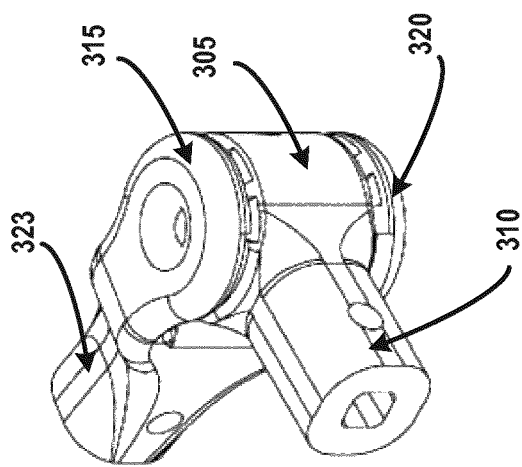
Figure 3B:
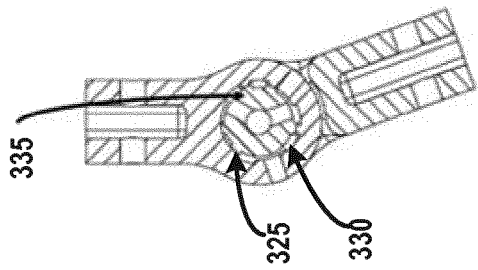
FIG. 3B shows an illustration of the hinge joint for the linkage assemblies in a deployed configuration, according to some embodiments.
Figure 3B:
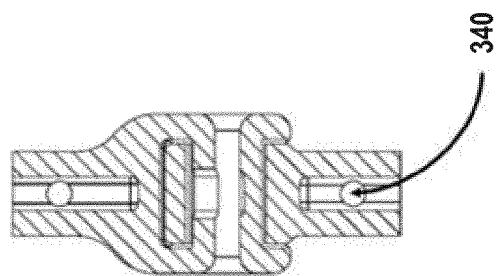
Figure 3B:
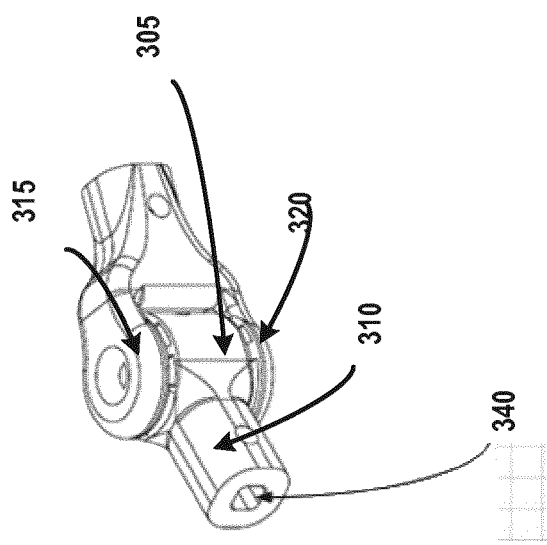

FIGS. 3A and 3B show illustrations of the hinge joint for the linkage assemblies, according to some embodiments. More specifically, FIG. 3A shows an external view, an internal side view and an internal top view of the hinge joint as it may be printed (e.g., using a 3D-printer generally known in the art), while FIG. 3B shows the same views for the hinge joint as it would be deployed. This example shows the joints of an arbitrary size, it being understood that the actual dimension of the joint can be scaled to suit the individual application and load capacity. A key design feature is that the hinge is printed in one configuration and used in another.

The hinge joint comprises an inner hinge member and an outer hinge member. The inner hinge member comprises a Follower Component 305 and a Cylindrical Joining Component 310. The outer hinge member comprises a Top Base Component 315, a Bottom Base Component 320, and a Cylindrical Joining Component 323. The Follower Component 305 interconnects with the outer hinge member between the Top Base Component 315 and the Bottom Base Component 320. Once interconnected, the inner hinge member can be rotated around a central axis with respect to the outer hinge member. Each Cylindrical Joining Component 310, 323 includes a channel for draining excess 3D printing material during printing (e.g., Channel 340). This also helps maintain a suitable maximal thickness for parts to prevent buildup of heat thus allowing for as little clearance as possible between parts.

As shown in the top internal view presented in FIG. 3A, the Follower Component 305 has a plurality of splines (e.g., Spline 325). The term "spline" as used herein refers to shapes (e.g., rectangles) on the interior part which fit into grooves in the outer part of the joint. These splines reside in grooves (e.g., Groove 330) on the Base component 315 and the Bottom Base Component 320. There is a Void 335 between the grooves and the splines providing a clearance (e.g., 0.5 mm) around both parts of the hinge.

In the deployed configuration, shown in FIG. 3B, the hinge rotates about its axis and at least three or more splines on Follower Component 305 are in contact with the outer wall of the joint provided by the Top Base Component 315 and the Bottom Base Component 320. In the example shown in FIG. 3B, there are five splines each making an 18° arc. These are spaced unevenly around the Follower Component 305. Likewise, the Top Base Component 315 and the Bottom Base Component 320 each have five matching grooves that line up with the inside part splines in the printing configuration. The Follower Component 305 can complete a certain number of degrees of rotation (e.g., 110 degrees) while maintaining a three spline contact. This is referred to herein as "the deployable range of motion for the joint." It may be noted that the dimensions of the inside spline arc, the number and location of the splines can be changed for each joint of the five bar mechanism such that the entire mechanism is printed with all the joints in the printing configuration. When the mechanism is assembled and is in its default position, the splines are in the center of their deployable range.

Figure 4A:
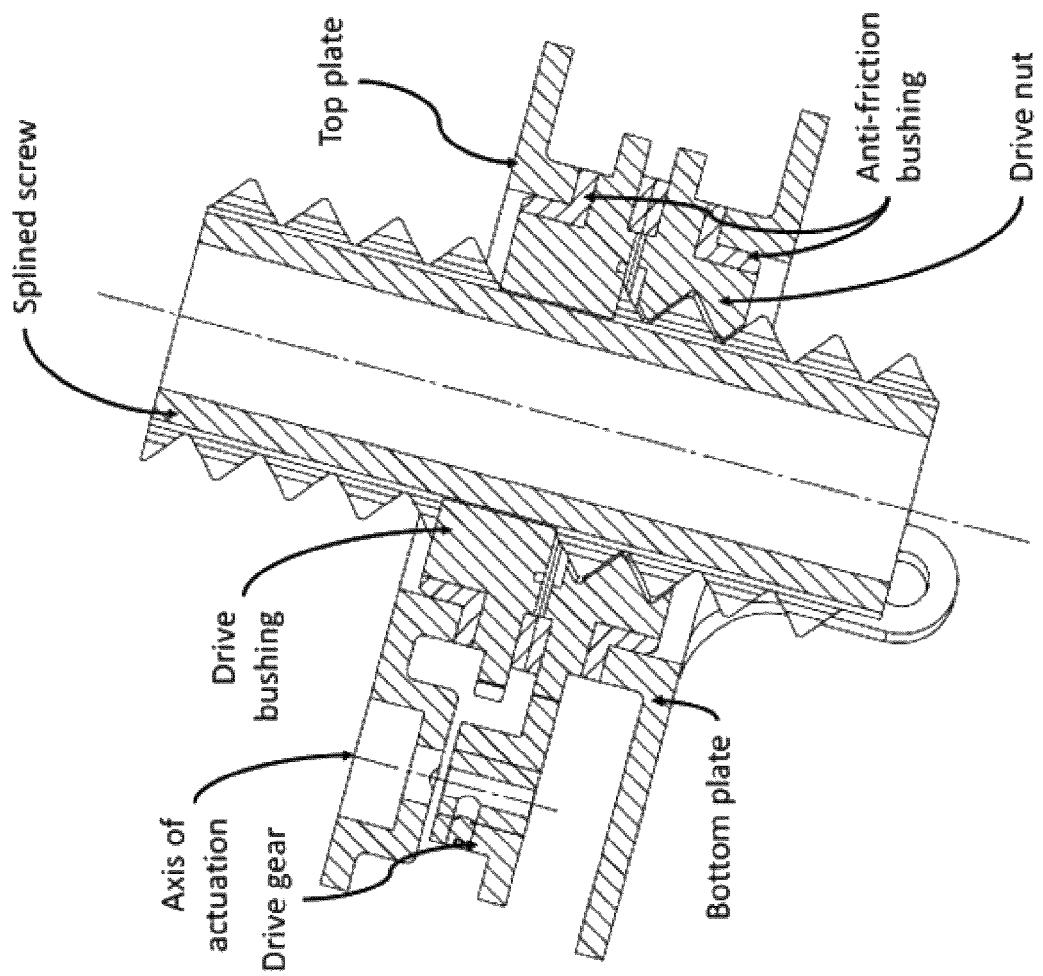
FIG. 4A illustrates a first view of the rotational and translational (RT) mechanism that is aligned with the insertion axis during operation, according to some embodiments.
Figure 4B:
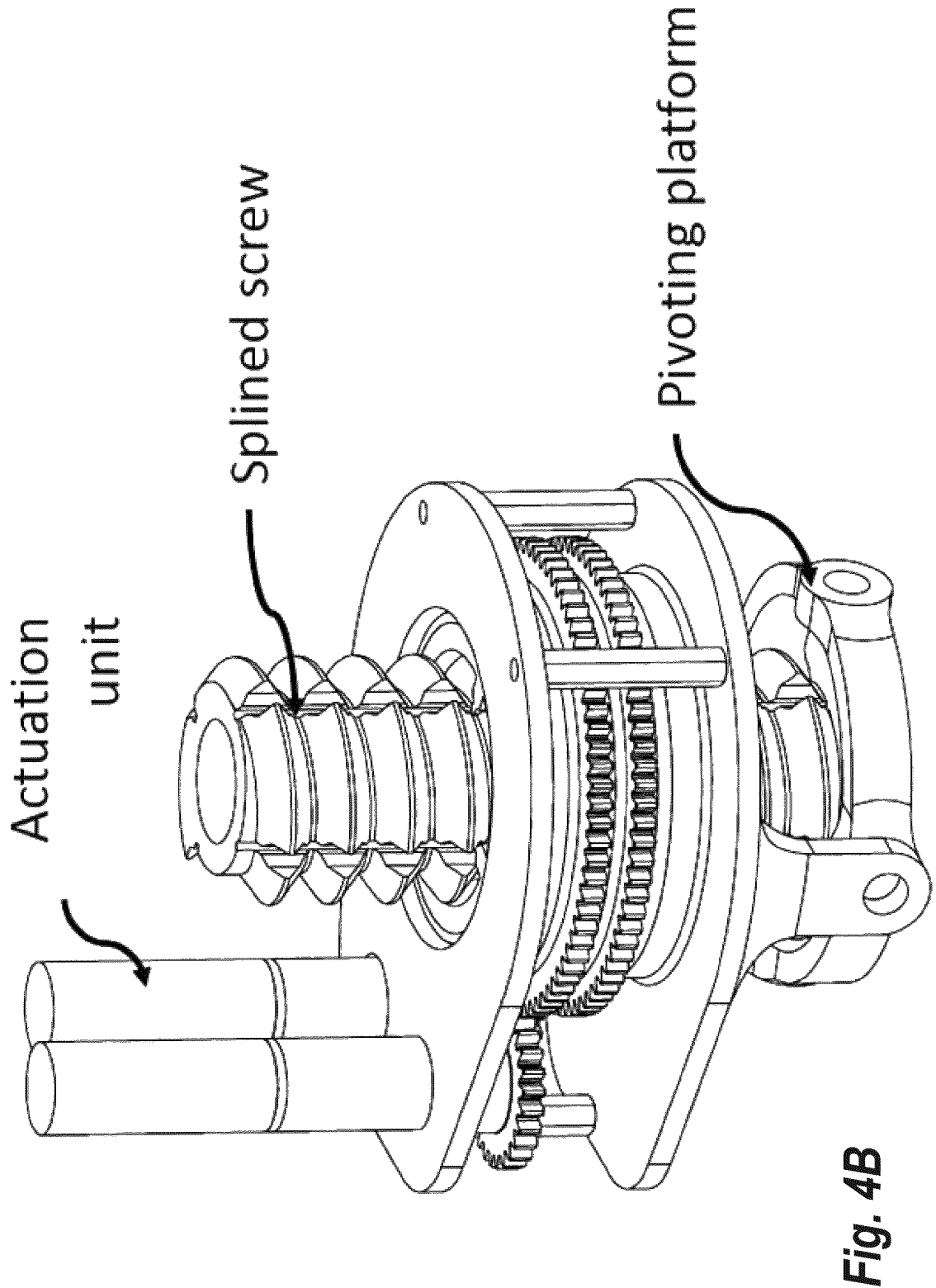
FIG. 4B illustrates a second view of the RT mechanism that is aligned with the insertion axis during operation, according to some embodiments.
Figure 4C:
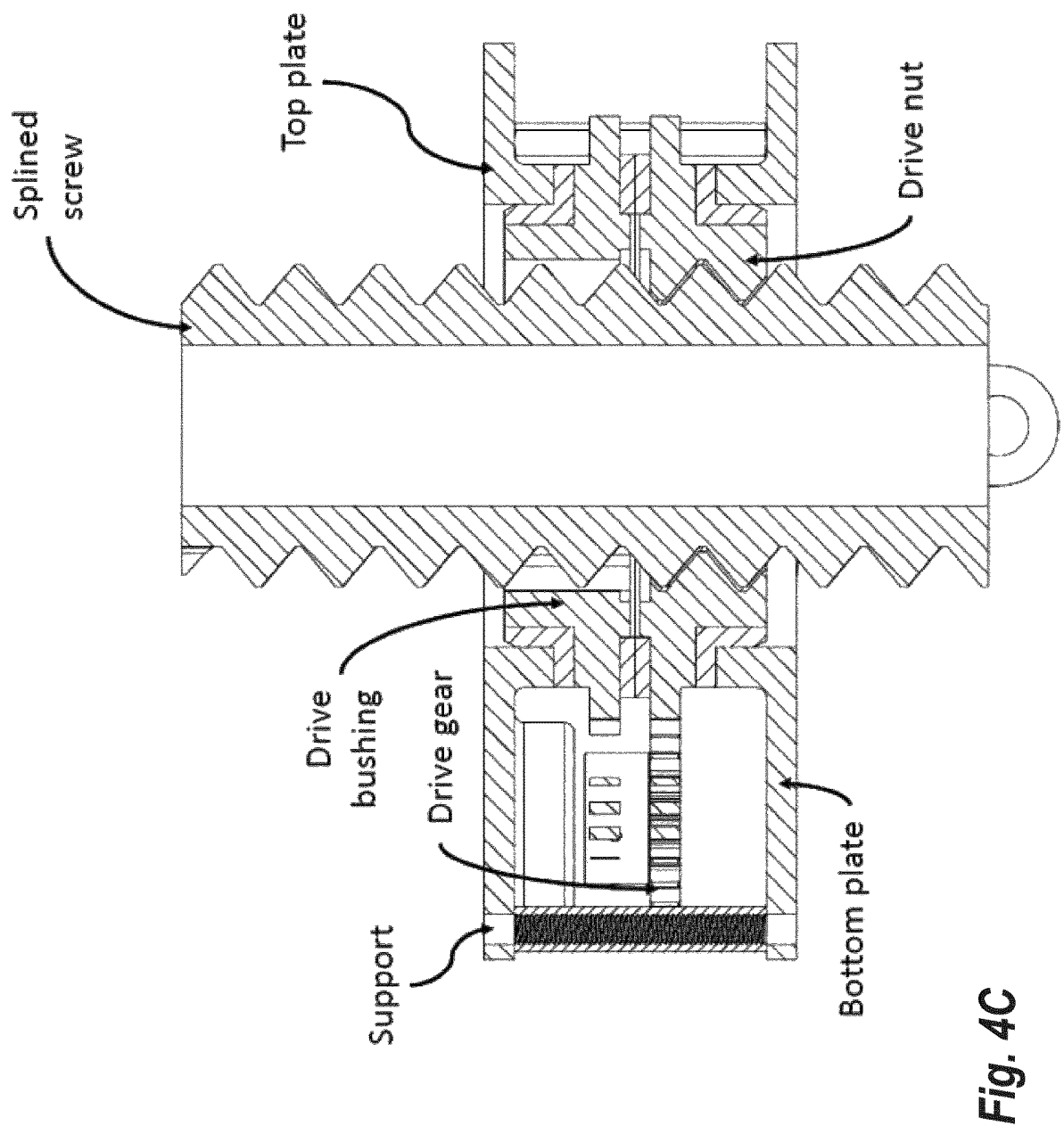
FIG. 4C illustrates a third view of the RT mechanism that is aligned with the insertion axis during operation, according to some embodiments.

FIGS. 4A, 4B, and 4C illustrate views of the RT mechanism that is aligned with the insertion axis during operation, according to some embodiments. The mechanism comprises a small set of components (detailed in the figures) that are mainly planar by themselves with the exception of a splined screw. That is, their thickness is small as compared to their lateral dimensions. This is required such that these components can be 3D printed with existing technologies without compromising the accuracy or functionality of the mechanism. The two supporting plates are separated by spacers. For embodiments that incorporate actuators in the RT mechanism, drive gears couple with the drive bushing and drive nut. Turning the drive bushing and the drive nut in opposite directions causes the splined screw to rotate about its axis. Turning the drive nut and drive busing in the same direction causes the splined screw to translate along its axis. For embodiments that power the RT mechanism via a cable or belt system, the drive nut and drive bushing are directly connected to the cable or belt. The gear teeth on the drive nut and drive bushing are replaced by cable grooves or sprocket teeth to mate with the respective power train mechanism. An anti-friction bushing made of suitable polymer such as Polytetrafluoroethylene or Ethylene tetrafluoroethylene may be used to provide a low coefficient of friction at low speeds and torques separates the drive nut and drive bushing from the top and bottom plates. Alternatively, the section of top and bottom plates in contact with the drive bushing and drive nut may be coated with anti-friction polymer after 3D printing.

Figure 5A:
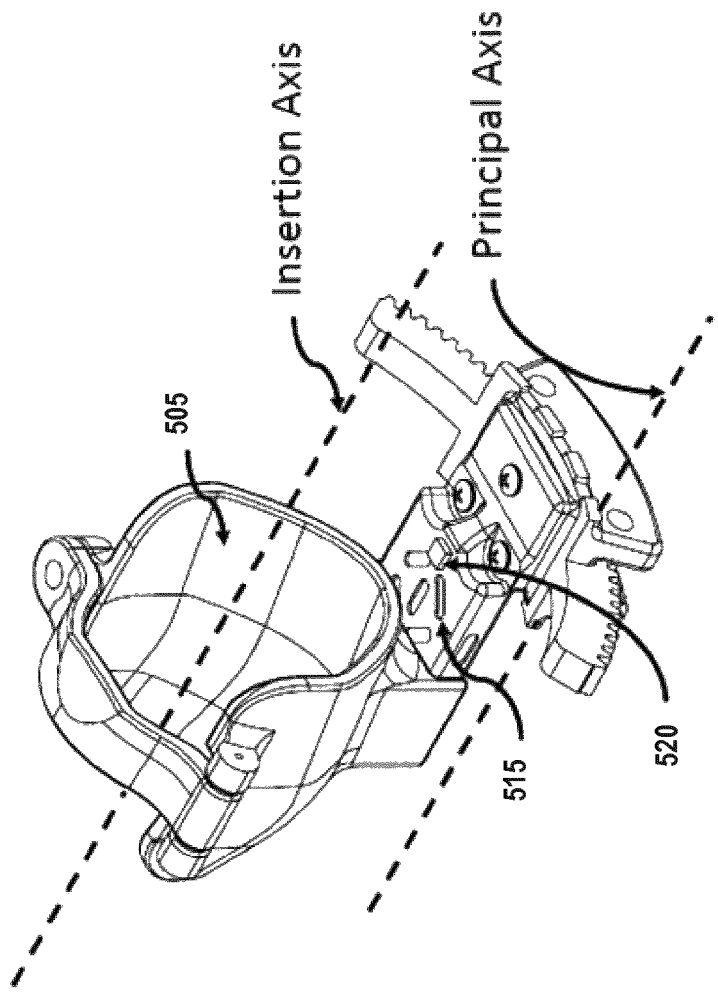
FIG. 5A shows an illustrative example where strain gauges and an inertial sensor are incorporated into the distal part of an end effector, according to some embodiments.
Figure 6:
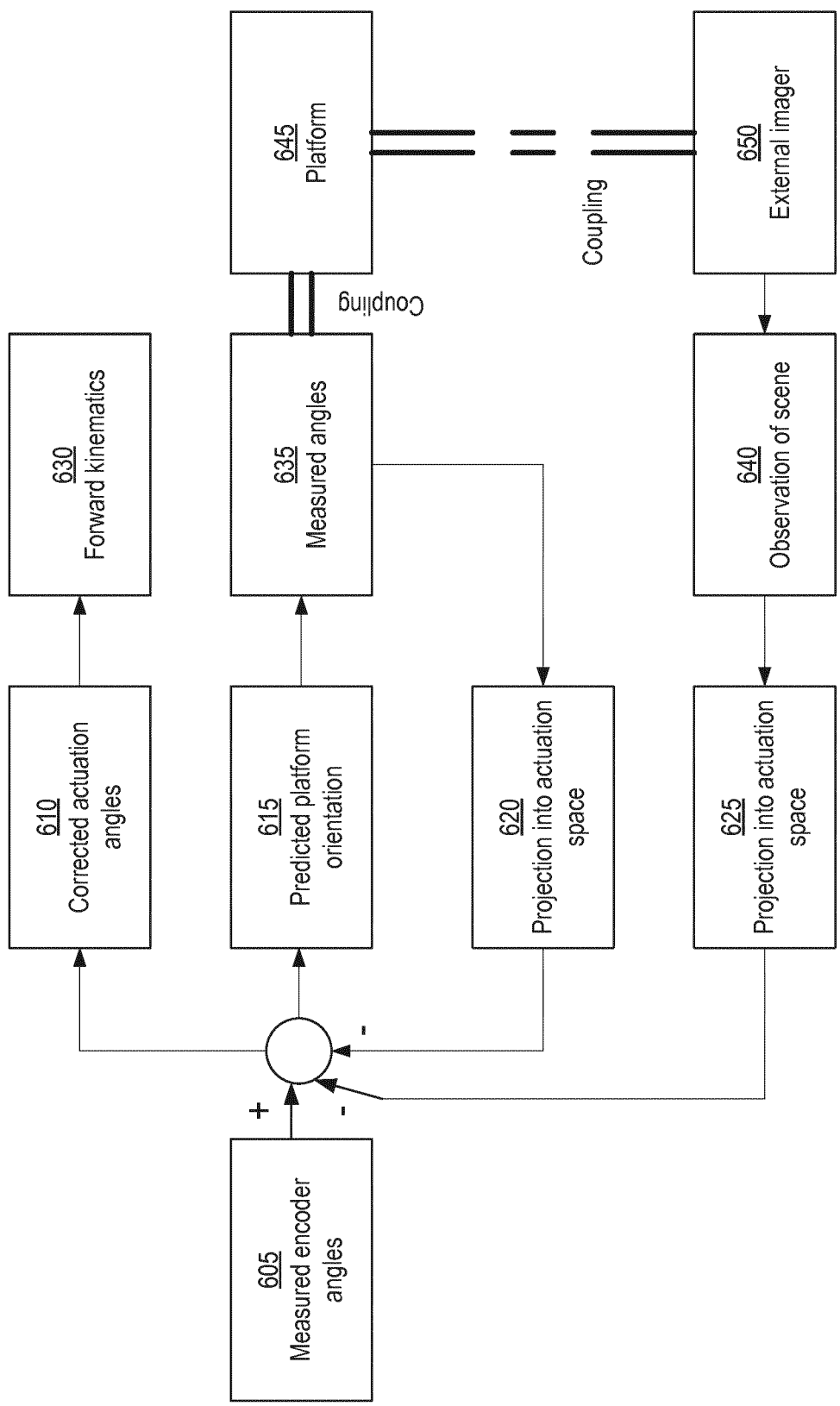
FIG. 6 provides a workflow for estimating the actuation angles which are then estimated using an estimator-corrector loop, according to some embodiments.

The current state-of-the-art of 3D printing techniques such as Stereolithography (SLA) or Selective Laser Sintering (SLS) produce parts of limited accuracy which is typically of the order of 0.3 mm. Thus, measurement of the actuation angles at the side of the motor would result in poor accuracy in determining the location of the end effector. To remedy this, Strain Gauges 515 and an Inertial Sensor 520 may be incorporated into the distal part of the End Effector 505 as shown in FIG. 5A. The actuation angles are then estimated using an estimator-corrector loop as illustrated in FIG. 6 (described below).

Figure 5B:
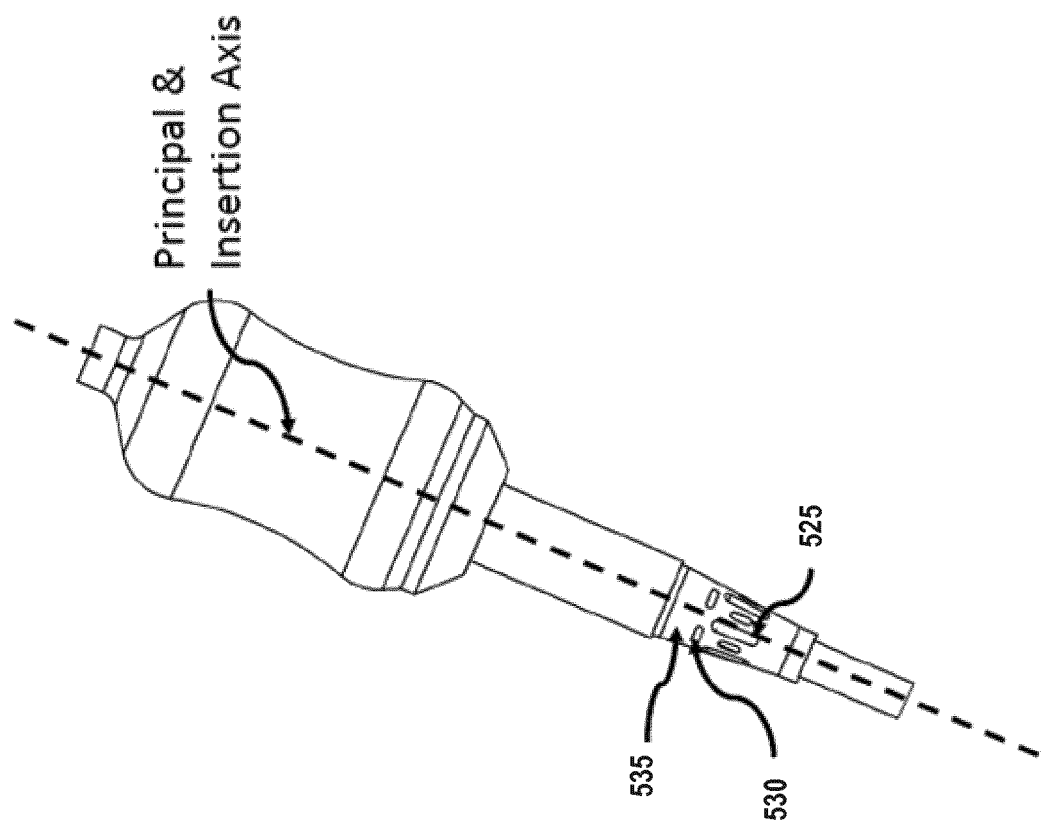
FIG. 5B shows an illustrative example of a handle force sensor that is built into the end effector holder when the insertion axis is not offset from the principal axis, as may be used in some embodiments.

FIG. 5B shows an illustrative example of a handle force sensor that is built into the end effector holder when the insertion axis is not offset from the Principal Axis. A number of Windows 525 or "strain concentrators" are modeled in this holder to concentrate the stress over bridges and measured using identical Strain Gauges 530. The holder is coupled to the RT mechanism using Coupling 535. In some embodiments, a redundant number (>6) of strain gauges are used. Such a redundancy improves accuracy as well as stability with temperature. If $v \in RS$ are the voltage readings from the S number of individual strain gauges, then the end effector wrench is given by:

$$\tau = F_e C v; C \in R^{6 \times S} \quad (1)$$

where $C \in R^{6 \times S}$ is a calibration matrix that is predetermined prior to the first use of the mechanism.

In some embodiments, the strain gauges are connected to a circuit board housed in the RT mechanism along with the inertial sensor. The voltage readings are digitized into a microcomputer in this circuit board and transformed into the end-effector wrench. These values along with the inertial sensor readings are communicated to the controller via a wireless interface. The low power wireless interface is preferred over cabling used in traditional robotic mechanism as this results in simpler design of the parts that can be fabricated without requiring individualized assembly. Unlike traditional robotic mechanisms, the mechanisms disclosed herein do not need to include channels for cabling to reduce size and complexity of design. For example, in embodiments that mount the actuators for the RT mechanism, the drive electronics for these two motors is also housed in the mechanism itself. These drive electronics can communicate with the main controller via wireless interface.

It is desirable in robots holding surgical instruments to be driven manually via collaborative control. The use of user force to control a robot in Cartesian space is generally understood by one skilled in the art and these techniques can be modified and supplemented with new features to further support the mechanisms discussed herein.

For example, some conventional techniques apply a scaling to the force input obtained via a force sensor attached to the end effector to determine the velocities of the robot in Cartesian space. Such a simplified control may not be possible in some embodiments of the present invention as there is coupling between the different actuation axis and the resultant motion of the end effector. Further, this coupling between the locations of Pivots 215F and 220F in FIG. 2A to the angulation, $m_i$, for motors i=1, 2 . . . 4 is nonlinear. To bridge this gap intermediate joint space may be utilized, which relates the angulation of the motor in actuation space to the location and orientation of the platform as well as the rotation and translation of the RT mechanism. The joint space has six degrees-of-freedom and is given by:

$$q = [d_1, d_2, \alpha_1, \alpha_2, \alpha_3, d_3]^t \in R^S \quad (2)$$

where $d_1$ and $d_2$ are the location of Pivot 220F.

In Equation 2, The angles $\alpha_1$ and $\alpha_2$ are orientation of the platform with respect to the ground plane. The angle $\alpha_3$ and distance $d_3$ are the roll and translation of the RT mechanism about its axis. Thus, the transformation of the end effector as a function of this joint space vector, q can be written as:

$$F(q) = T(I, [d_1, d_2, 0]^t) \times T(R(\hat{x}, \alpha_1), 0) \times T(R(\hat{y}, \alpha_2), 0) \times T(I, [0, 0, d_3]^t) \times T(R(\hat{z}, \alpha_3), 0) \quad (3)$$

where $T(R(\bullet), P)$ is a $4 \times 4$ homogeneous transformation matrix with rotation $R(\bullet) \in SO(3\in)$ and translation $P \in \mathcal{R}^3$. The identity matrix is I and $R(\hat{a}, \mathcal{B})$ is a rotation matrix about an axis $\hat{a}$ by angle $\mathcal{B}$. The location of Pivot 220F is a function of motor angles 3 and 4, and link length vector $L_b = l_{b0}, \ldots, l_{b4}$ (i.e., the length of links in Linkage B shown in FIG. 2A). The location of Pivot 215F, $p_{4b}$ is a function of motor angles 1 and 2, and the link length vector $L_a$ (i.e., the length of links in Linkage B shown in FIG. 2A). Without loss of generality, we shall assume that $L_a = L_b = L$. Thus:

$$p_{4a} = F_5(m_1, m_2, L) \text{ and } p_{4b} = F_5(m_3, m_4, L) \quad (4)$$

Thus, the relationship between $d_1$, $d_2$, $\alpha_1$, $\alpha_2$ and the actuation angles $m_1, \ldots, m_4$ is given by:

$$d_1 = p_{4b}(x) \quad (5)$$

$$d_2 = p_{4b}(y) \quad (6)$$

$$\alpha_1 = \arctan(o_{4a}(y) - p_{4b}(y), d) \quad (7)$$

$$\alpha_2 = \arctan(p_{4a}(y) - p_{4b}(y), p_{4a}(x) - p_{4b}(x)) \quad (8)$$

where $p(b)$, $b \in x, y$ are the x and y coordinates of the point. The relationship between $\alpha_3$, $d_3$ and actuation angles $m_5$, $m_6$ is given by a coupling matrix A dependent on the pitch of the screw as:

$$[\alpha_3, d_3]^t = A[m_t, m_6]^t \quad (9)$$

Equations 3-8 together provide the non-linear vector valued function, $F_{mq}$ that relates the actuation space, $m = [m_1, \ldots m_6]^t \in \mathcal{R}^6$ to joint space $q \in \mathcal{R}^6$. Taking the derivative of this vector valued function results in a Jacobian $J_{mq}$ that relates the joint velocities $\dot{q}$ to the actuator velocities $\dot{m}$. This can be written as:

$$q = F_{mq}(m_1, \ldots, m_6, L, d, A) \text{ and } \dot{q} = J_{mq}\dot{m} \quad (10)$$

$$\text{where } J_{mq} = \begin{bmatrix} \frac{\partial q_1}{\partial m_1} & \cdots & \frac{\partial q_6}{\partial m_1} \\ \vdots & \ddots & \vdots \\ \frac{\partial q_1}{\partial m_6} & \cdots & \frac{\partial q_6}{\partial m_6} \end{bmatrix} \in \mathcal{R}^{6 \times 6}$$

The relationship between the joint velocities $\dot{q}$ and the Cartesian velocities $\dot{x}$ can be derived from the derivative of Equation (3). Having established this relationship bridges the gap to enable collaborative control of the robot based on controlling the actuation velocities based on the measured sensor readings. That is:

$$\dot{m} = (J_{qx}J_{mq})^+ \text{diag}(k)\tau \quad (11)$$

where $\tau$ is the measured wrench (force/torque) at the handle, $k \in \mathcal{R}^6$ is a scaling term and $(\bullet)^+$ is the Moore-Penrose pseudo-inverse of the matrix. In some embodiments, the pseduo-inverse may be used to ensure that the actuation velocities remain stable even near singular points of the matrix $J_{qx}J_{mq}$. For locking a particular degree of freedom in Cartesian space, one could either assign $\tau$ to zero or set element in k to zero. Both of these could be triggered when the user has specified to lock the system.

Some embodiments of the present invention employ image based constrained control of the robot as a technique to achieve the desired behavior for a robotic holder. A constrained control of the robot can be written as follows:

$$\underset{\dot{q}}{\text{minimize}} \sum g_i(\dot{q}, x_i^d) \quad (12)$$

$$\text{subject to } c_j(\dot{q}, x_i^d) = 0$$

where $g_i$ and $c_j$ are functions that relate Cartesian motion to joint motions. The same notation may be adapted to extend the control to image derived control. Specifically, the concept of image Jacobian may be applied to constraint control. Note that Image Jacobian is generally known in the art; however, in conventional approaches, the set points for the controller are also set in image space. With the techniques described herein, both image space and Cartesian space constraints are applied towards restricting the motions in specific directions based on the derived constraints. The remaining unrestricted image or Cartesian space is controlled by desired input that typically enables compliance of the ultrasound probe in the unrestricted space.

If f is set of observed features in the image space, including the vectorization of the entire image, $\dot{f}$ is the corresponding vector of rate of change of image features. Then, the image Jacobian is the linear mapping from the tangent space of $x_k$, the Cartesian pose of any arbitrary coordinate frame attached to the robot to the tangent space of the features, that is $\dot{f} = J_I \dot{x}_k$. If we apply the manipulator Jacobian to this equation, then:

$$\dot{f} = J_I J_{kq} J_{mq} \dot{m} \quad (13)$$

provides the linearized relationship between Cartesian pose of the kth coordinate frame to rate of change of actuation space. Using this image Jacobian, a formulation for Equation 13, can be written as:

$$\underset{\dot{q}}{\text{minimize}} |\dot{x}_i - J_i \dot{q}|_m + \sum_{j=1}^{N} |\dot{x}_j^o - J_j \dot{q}|_m + \alpha^t s_I + \beta^t s_t \quad (14)$$

$$\text{subject to } |\dot{x}_k - J_I J_k \dot{q}|_m \le \varepsilon_I + s_I \quad \forall k = 1, \ldots, M$$

$$|\dot{x}_t - J_t \dot{q}|_m \le \varepsilon_t + s_t \quad \forall t = 1, \ldots, P$$

where $J_k$, $J_t$, $J_i$ and $J_j$ are manipulator Jacobians for frames k, t, i and j, respectively. $J_I$ is the image Jacobian. The Cartesian velocities for frames k, t, i, and j are given by $\dot{x}_k$, $\dot{x}_t$, $\dot{x}_i$, $\dot{x}_j$, respectively. The superscript d and o points to the desired velocities of the handle frame i and the objective required to me meet for frames j, respectively. In the above formulation, there are P task based constraints, M image based constraints and N objectives to be meet in addition to desired motion for the handle of transducer. Obviously, one can add slack variables, $s_I$ and $s_t$ to relax the constraints and control the degree of slackness by parameters $\alpha$ and $\beta$, respectively. The norm operator, $|\bullet|_m$ can be any of L1, L2 or L2 norm squared or a combination thereof.

In conventional systems, the constraints are either formulated as linear or nonlinear constraints. For example, in some conventional, techniques the nonlinear constraints where solved by feasible sequential quadratic programs, which would locally convert the nonlinear constraints into a series of iterative quadratic programs while ensuring the solution always remains in the feasible set. However, as an alternative to this technique, various embodiments of the present invention directly solve a second-order cone programming (SOCP). The objective can be any convex form of L1, L2 or L2 norm squared. Since the minimum for each is the same, one can act as surrogate of other. It is possible to solve this problem in the rates required for robot control (e.g., approximately 10 ms) with algorithms similar to embedded conic solver (ECOS) which use interior point methods for SOCP. This difference results in no trade-offs to be made between speed and accuracy as no linearization is made for the constraints. In earlier conventional approaches, a trade-off had to be made between speed (linear constraint methods) and accuracy (non-linear constraints).

FIG. 6 provides a workflow for estimating the actuation angles which are then estimated using an estimator-corrector loop, according to some embodiments. Platform 645 is coupled directly or indirectly to an External Imaging 650. The Measured Encoder Angles 605 are used to determine a Predicted Platform Orientation 615. This Predicted Platform Orientation 615 is combined with Measured Angles 635 (measured using an inertial sensor on the Platform 645) to generate a Projection 620 which represents a projection of the angles into actuation space. The Observation of the Scene 640 is acquired from the External Imager 650 and projected into actuation space to yield Projection 625. Using the Measured Encoder Angles 605 and the two Projections 620, 625, Corrected Actuation Angles 610 are determined which, in turn, are used to determine Forward Kinematics 630.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A system for holding and controlling medical instruments during procedures, the system comprising:
   an end effector configured to hold a medical instrument;
   a rotational and translational (RT) mechanism configured to rotate and translate the medical instrument along an insertion axis;
   a platform coupled to the RT mechanism;
   a pair of parallel five-bar planar linkages configured to translate, pitch, and yaw the platform with respect to a principal axis that is parallel to the insertion axis; and
   a motor box comprising a plurality of motors configured to provide motion inputs to the pair of parallel five-bar planar linkages,
   wherein the motion inputs are provided to the RT mechanism using a cable or belt running parallel to the pair of parallel five-bar planar linkages,
   wherein the system is grouped in two sub-assemblies comprising:
      a first sub-assembly of reusable parts comprising the end effector, the RT mechanisms, and the platform, and
      a second sub-assembly of disposable parts comprising the pair of parallel five-bar planar linkages.

2. The system of claim 1, further comprising:
   an inertial sensor embedded in the platform or the end effector, and
   a set of strain gauges mounted on a coupling between the end effector and the RT mechanism,
   wherein the system is controlled based on one or more of user input received via the strain gauges and measurements received via the inertial sensor.

3. The system of claim 1, wherein the end effector, the RT mechanisms, the platform, and the pair of parallel five-bar planar linkages are fabricated using additive manufacturing techniques.

4. The system of claim 1,
   wherein the first sub-assembly and the second sub-assembly are joined via a magnetically power rapid connect-disconnect coupling.

5. The system of claim 1, further comprising:
   one or more additional motors mounted on the platform and configured to provide the motion inputs to the RT mechanism.

6. The system of claim 5, wherein the motor box is coupled to one or more other components of the system using a magnetic powered quick connect-disconnect mechanism.

7. The system of claim 1, further comprising:
   an external imager configured to acquire one or more images during the procedure,
   wherein the system is controlled at least in part using the one or more images.

8. The system of claim 1, wherein each of the planar five-bar linkages comprise a plurality of hinge joints and wherein each hinge joint comprises:
   an inner hinge member comprising:
      a follower component, and
      a plurality of splines spaced around a top of the follower component and a bottom of the follower component;
   an outer hinge member comprising:
      a top base component comprising a first set of grooves distributed around an interior portion of the top base component, and
      a bottom base component comprising a second set of grooves distributed around an interior portion of the bottom base component; and
   wherein the follower component interconnects with the outer hinge member, and the follower component is located between the top base component and the bottom base component when in a printed configuration or a deployed configuration, and
   wherein the first set of grooves and the second set of grooves are spaced such that (a) the splines align with the grooves when the hinge joint is in the printed configuration and (b) the splines do not align with the grooves when the hinge joint is in the deployed configuration.

9. A system for holding and controlling medical instruments during procedures, the system comprising: a first assembly of 3D printed components comprising: an end effector configured to hold a medical instrument; a rotational and translational (RT) mechanism configured to rotate and translate the medical instrument along an insertion axis; a motor box comprising a plurality of motors configured to provide motion inputs to a pair of parallel five-bar linkages; a platform coupled to the RT mechanism; and a second assembly of 3D printed components comprising the pair of parallel five-bar linkages configured to translate, pitch, and yaw the platform with respect to a principal axis that is parallel to the insertion axis, wherein the system is grouped in two sub-assemblies comprising: a first sub-assembly of reusable parts comprising the end effector, the RT mechanisms, and the platform, and a second sub-assembly of disposable parts comprising the pair of parallel five-bar linkages, wherein the first assembly is coupled to the second assembly using a magnetic powered quick connect-disconnect mechanism, wherein the motion inputs are provided to the RT mechanism using a cable or belt running parallel to the pair of parallel five-bar linkages.

10. The system of claim 9, wherein each five-bar linkage is a planar linkage.

11. The system of claim 9, wherein each five-bar linkage is a spherical linkage.

12. The system of claim 9, wherein each of the five-bar linkages comprise a plurality of links and a plurality of hinge joints capable of being printed as a single unit in a printed configuration and used as the single unit in a deployed configuration.

* * * * *